United States Patent
Teuber et al.

[11] Patent Number: 5,922,725
[45] Date of Patent: Jul. 13, 1999

[54] BENZIMIDAZOLE COMPOUNDS AND THEIR USE AS MODULATORS OF THE GABA$_A$ RECEPTOR COMPLEX

[75] Inventors: Lene Teuber, Vaerlose; Frank Wätjen, Herlev, both of Denmark; Yoshimasa Fukuda, Yokohama, Japan; Osamu Ushiroda, Yokohama, Japan; Toshiro Sasaki, Yokohama, Japan

[73] Assignees: Neurosearch A/S, Glostrup, Denmark; MeijI Seika Kaisha, Ltd., Tokyo, Japan

[21] Appl. No.: 08/945,123

[22] PCT Filed: Apr. 19, 1996

[86] PCT No.: PCT/EP96/01649

§ 371 Date: Dec. 23, 1997

§ 102(e) Date: Dec. 23, 1997

[87] PCT Pub. No.: WO96/33191

PCT Pub. Date: Oct. 24, 1996

[30] Foreign Application Priority Data

Apr. 21, 1995 [DK] Denmark .................. 0460/95
Jun. 27, 1995 [DK] Denmark .................. 0741/95

[51] Int. Cl.$^6$ ............... C07D 401/10; C07D 403/10; C07D 405/10; C07D 409/10; C07D 417/10; A61K 31/415

[52] U.S. Cl. .................. 514/256; 514/307; 514/314; 514/333; 514/338; 514/394; 544/331; 544/333; 546/273.4; 546/269.4; 546/304; 546/144; 548/126; 548/305.1; 548/305.4; 548/306.1

[58] Field of Search ............ 546/273.4; 548/305.1, 548/305.4; 514/338, 394, 333, 307, 256, 314; 544/333, 331

[56] References Cited

U.S. PATENT DOCUMENTS 5,158,969 10/1992 Olesen et al. ................ 514/419
5,360,809 11/1994 Axelsson et al. ............. 514/338
5,554,632  9/1996 Teuber et al. ............... 514/338

FOREIGN PATENT DOCUMENTS 0520200 12/1992 European Pat. Off. .
0563001  3/1993 European Pat. Off. .

*Primary Examiner*—Floyd D. Higel
*Attorney, Agent, or Firm*—Birch, Stewart, Kolasch & Birch, LLP

[57] ABSTRACT

The present patent application discloses compounds having the formula

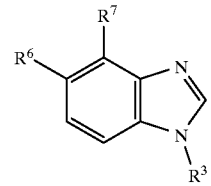

or a pharmaceutically acceptable salt thereof or an oxide thereof wherein $R^3$ is

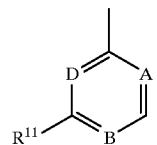

wherein A, B and D each is CH, or one or two of A, B and D is N and the others are CH;

$R^{11}$ is phenyl, benzimidazolyl, or monocyclic heteroaryl, all of which may be substituted one or more times with substituents selected from alkyl, alkoxy, halogen, $CF_3$, amino, nitro, cyano, acylamino, acyl, phenyl and monocyclic heteroaryl;

one of $R^6$ and $R^7$ is hydrogen and the other is —CR'=NOR", wherein R' and R" each independently are hydrogen, alkyl, alkenyl, alkynyl or phenyl.

The compounds are useful for the treartment of various central nervous system disorders such as epilepsy and other convulsive disorders, anxiety, sleep disorders and memory disorders.

14 Claims, 5 Drawing Sheets

Figure 1a:

Hal is halogen, alk is alkyl, and A, B, D, have the meanings set forth in the claims.

Figure 1b:

Hal is halogen and A, B, D, R" and $R^{11}$ is as defined in the claims

Figure 2:

A, B, D, R', R" and R[11] is as set forth in the

Figure 3

Hal is halogen, A,B,D, R',R" and R[11] is as set forth in the claims

Figure 4:

Hal is halogen, A, B, D, R" and R[11] is as defined in the claims.

BENZIMIDAZOLE COMPOUNDS AND THEIR USE AS MODULATORS OF THE GABA$_A$ RECEPTOR COMPLEX

This application claims priority on PCT International Application PCT/EP96/01649 which has an International filing date of Apr. 19, 1996, which designated the Unites States of America.

This invention relates to novel benzimidazole compounds, pharmaceutical compositions containing these compounds, methods of treating therewith, and to method of preparing such benzimidazole compounds. The novel compounds are useful in the treatment of central nervous system diseases and disorders, which are responsive to modulation of the GABA$_A$ receptor complex, such as for example anxiety, sleep disorders, memory disorders, and epilepsia or other convulsive disorders,

BACKGROUND OF THE INVENTION

Receptors for γ-aminobutyric acid (GABA), GABA$_A$ receptors are the most abundant inhibitory receptors in mammalian brain. The GABA$_A$ receptor are structurally constituted as macromolecular heteropentameric assemblies (combinations of a, and γ/δ protein subunits). Several subtypes of such GABA$_A$ receptors have been described by techniques of modern molecular biology. Each GABA$_A$ receptor complex comprises a chloride ion channel that controls chloride flux across the neuronal membrane, and multiple recognition sites for small modulatory molecules such as benzodiazepines, barbiturates, picrotoxin, and certain steroids. When GABA interacts with its receptor, the ion channel is opened, chloride influx is enhanced, the membrane is hyperpolarized and the cell becomes less responsive to excitatory stimuli. This GABA induced ion current can be regulated by diverse agents, including agents that interact with the benzodiazepine receptor or recognition site.

Agents that bind or interact with the modulatory sites on the GABA$_A$ receptor complex, such as for example the benzodiazepine receptor, can have either enhancing effect on the action of GABA, i.e. a positive modulatory effect of the receptor (agonists, partial agonists), an attenuating effect on the action of GABA, i.e. negative modulation of the receptor (inverse agonists, partial inverse agonists), or they can block the effect of both agonists and inverse agonists by competitive block (antagonists or ligands without intrinsic activity).

Agonists generally produce muscle relaxant, hypnotic, sedative, anxiolytic, and/or anticonvulsant effects, while inverse agonists produce proconvulsant, anti-inebriant, and anxiogenic effects. Partial agonists are characterized as compounds with anxiolytic effects but without or with reduced muscle relaxant, hypnotic and sedative effects, whereas partial inverse agonists are considered to be useful as cognition enhancers.

Numerous compounds belonging to different series of compounds having affinity for the benzodiazepine receptors have been synthesized during the last three decades. However, although the benzodiazepine receptor sites are still considered as very attractive biological sites for interfering with the CNS to treat various disorders and diseases, then nearly all previously synthesized compounds acting at these receptor sites have failed during clinical development because of unacceptable side effects.

The present invention provides novel benzimidazole compounds that interact with the benzodiazepine receptor of the GABA$_A$ receptor complex. The compounds of the present invention are valuable modulators of the GABA$_A$ receptor complex.

OBJECT OF THE INVENTION

It is an object of the present invention to provide novel benzimidazole compounds and pharmaceutically-acceptable acid addition salts thereof, which are useful in the treatment of central nervous system disorders, diseases or ailments, which are responsive to the modulation of the GABA$_A$ receptor complex, and especially the positive modulation of the GABA$_A$ receptor complex.

Another object of the present invention is to provide pharmaceutical compositions comprising the novel benzimidazole compounds being useful for the above purposes. Still another object of the present invention is to provide a novel method of treating with the novel benzimidazole compounds.

A further object of the present invention is to provide a method of preparing the novel pharmaceutical compositions.

Additional objects will be obvious from the following description, and others will be obvious to one skilled in the art.

SUMMARY OF THE INVENTION

The invention then, inter alia, comprises the following, alone or in combination: A compound having the formula:

or a pharmaceutically acceptable salt thereof or an oxide thereof
wherein
$R^3$ is wherein
A, B and D each is CH, or one or two of A, B and D is N and the others are CH;
$R^{11}$ is phenyl, benzimidazolyl, or monocyclic heteroaryl, all of which may be substituted one or more times with substituents selected from alkyl, alkoxy, halogen, $CF_3$, amino, nitro, cyano, acylamino, acyl, phenyl and monocyclic heteroaryl;
one of $R^6$ and $R^7$ is hydrogen and the other is —CR'═NOR", wherein R' and R" each independently are hydrogen, alkyl, alkenyl, alkynyl or phenyl;
a compound as above, which is
1-(3-(3-furanyl)-phenyl)-5-formyl-benzimidazole O-methyl oxime,
5-acetyl-1-(3-(3-pyridyl)phenyl)benzimidazole O-ethyl oxime,
5-acetyl-1-(3-(3-pyridyl)phenyl)benzimidazole oxime,
5-acetyl-1-(3-(1-imidazolyl)phenyl)benzimidazole O-methyl oxime,
5-acetyl-1-(3-(1-imidazolyl)phenyl)benzimidazole O-ethyl oxime, or
5-acetyl-1-(3-(2-thiazolyl) phenyl)benzimidazole O-methyl oxime, or a pharmaceutically acceptable salt thereof or an oxide thereof;
a pharmaceutical composition comprising an effective amount of a compound as any above or a pharmaceutically acceptable salt thereof or an oxide thereof together with at least one pharmaceutically acceptable carrier or diluent;

the use of a compound as any above for the preparation of a medicament for the treatment of a disorder or disease of a living animal body, including a human, which disorder or disease is responsive to the modulation of the $GABA_A$ receptor complex of the central nervous system;

the use of a compound as any above for the preparation of a medicament for the treatment of a disorder or disease of a living animal body, including a human, which disorder or disease is responsive to positive modulation of the $GABA_A$ receptor complex of the central nervous system;

the use of a compound as any above for the preparation of a medicament for the treatment of a disorder or disease selected from anxiety, sleep disorders, memory disorders, epilepsy or any other convulsive disorder;

a method of treating a disorder or disease of a living animal body, including a human, which disorder or disease is responsive to modulation of the $GABA_A$ receptor complex of the central nervous system comprising administering to such a living animal body, including a human, in need thereof a therapeutically effective amount of a compound as any above;

the method as above, wherein a disorder or disease responsive to positive modulation of the $GABA_A$ receptor complex is treated;

the method as above, wherein anxiety, sleep disorders, memory disorders, epilepsy or any other convulsive disorder is treated; and the method as above, wherein the active ingredient is administered in form of a pharmaceutical composition thereof, in which it is present together with a pharmaceutically acceptable carrier or diluent.

Halogen is fluorine, chlorine, bromine, or iodine.

Alkyl means a straight chain or branched chain of from one to eight carbon atoms or cyclic alkyl of from three to seven carbon atoms, including but not limited to, methyl, ethyl, propyl, isopropyl, butyl, isobutyl, t-butyl, pentyl, hexyl, cyclopropyl, cyclobutyl, cyclopentyl, cyclohexyl; methyl, ethyl, propyl, isopropyl and t-butyl are preferred groups.

Alkenyl means a straight chain or branched chain of from two to six carbon atoms containing one double bond, including but not limited to ethenyl, 1-propenyl, 2-propenyl, 1-butenyl, 2-butenyl, and 3-butenyl.

Alkynyl means a straight chain or branched chain of from two to six carbon atoms containing one triple bon, including but not limited to ethynyl, 1-propynyl, 2-propynyl, 1-butynyl, 2-butynyl, and 3-butynyl.

Alkoxy means O-alkyl, wherein alkyl is as defined above.

Acyl means —(C=O)—H or —(C=O)—alkyl, wherein alkyl is as defined above.

Acylamino is acyl—NH— wherein acyl is as defined above.

Amino is —$NH_2$ or —NH—alkyl or —N—$(alkyl)_2$, wherein alkyl is as defined above.

Monocyclic heteroaryl is a 5- or 6-membered heterocyclic monocyclic group. Such a monocyclic heteroaryl group includes, for example, oxazol-2-yl, oxazol-4-yl, oxazol-5-yl, isoxazol-3-yl, isoxazol-4-yl, isoxazol-5-yl, thiazol-2-yl, thiazol-4-yl, thiazol-5-yl, isothiazol-3-yl, isothiazol-4-yl, isothiazol-5-yl, 1,2,4-oxadiazol-3-yl, 1,2,4-oxadiazol-5-yl, 1,2,4-thiadiazol-3-yl, 1,2,4-thiadiazol-5-yl, 1,2,5-oxadiazol-3-yl, 1,2,5-oxadiazol-4-yl, 1,2,5-thiadiazol-3-yl, 1,2,5-thiadiazol-4-yl, 1-imidazolyl, 2-imidazolyl, 4-imidazolyl, 1-pyrrolyl, 2-pyrrolyl, 3-pyrrolyl, 2-furanyl, 3-furanyl, 2-thienyl, 3-thienyl, 2-pyridyl, 3-pyridyl, 4-pyridyl, 2-pyrimidinyl, 4-pyrimidinyl, 5-pyrimidinyl, 3-pyridazinyl, 4-pyridazinyl, 2-pyrazinyl, 1-pyrazolyl, 3-pyrazolyl, and 4-pyrazolyl.

Examples of pharmaceutically-acceptable addition salts include inorganic and organic acid addition salts such as the hydrochloride, hydrobromide, phosphate, nitrate, perchlorate, sulphate, citrate, lactate, tartrate, maleate, fumarate, mandelate, benzoate, ascorbate, cinnamate, benzenesulfonate, methanesulfonate, stearate, succinate, glutamate, glycollate, toluene-p-sulphonate, formate, malonate, naphthalene-2-sulphonate, salicylate and the acetate for example.

Other acids such as oxalic acid, while not in themselves pharmaceutically acceptable may be useful in the preparation of salts useful as intermediates in obtaining compounds of the invention and their pharmaceutically acceptable acid addition salts. Such salts are formed by procedures well known in the art.

Further, the compounds of this invention may exist in unsolvated as well as in solvated forms with pharmaceutically acceptable solvents such as water, ethanol and the like. In general, the solvated forms are considered equivalent to the unsolvated forms for the purposes of this invention.

Some of the compounds of the present invention exist in (+) and (−) forms as well as in racemic forms. Racemic forms can be resolved into the optical antipodes by known methods, for example, by separation of diastereomeric salts thereof, with an optically active acid, and liberating the optically active amine compound by treatment with a base. Another method for resolving racemates into the optical antipodes is based upon chromatography on an optical active matrix. Racemic compounds of the present invention can thus be resolved into their optical antipodes, e.g., by fractional crystallization of d- or l- (tartrates, mandelates, or camphorsulphonate) salts for example. The compounds of the instant invention may also be resolved by the formation of diastereomeric amides by reaction of the compounds of the present invention with an optically active activated carboxylic acid such as that derived from (+) or (−) phenylalanine, (+) or (−) phenylglycine, (+) or (−) camphanic acid or by the formation of diastereomeric carbamates by reaction of the compounds of the present invention with an optically active chloroformate or the like.

Additional methods for the resolvation of optical isomers, known to those skilled in the art may be used, and will be apparent to the average skilled in the art. Such methods include those discussed by J. Jaques, A. Collet, and S. Wilen in "Enantiomers, Racemates, and Resolutions", John Wiley and Sons, New York (1981).

Furthermore, as the compounds of the invention are oximes they can exist in two forms, Z- and E-form, depending on the arrangement of the substituents around the —C=N— double bond. The present invention includes both the Z- and E-form of the compounds of the invention as well as mixtures thereof.

The compounds of the invention may be prepared in numerous ways.

The compounds of the invention and their pharmaceutically acceptable derivatives may thus be prepared by any method known in the art for the preparation of compounds of analogous structure and as shown in the representative examples which follows.

Figure 1A:
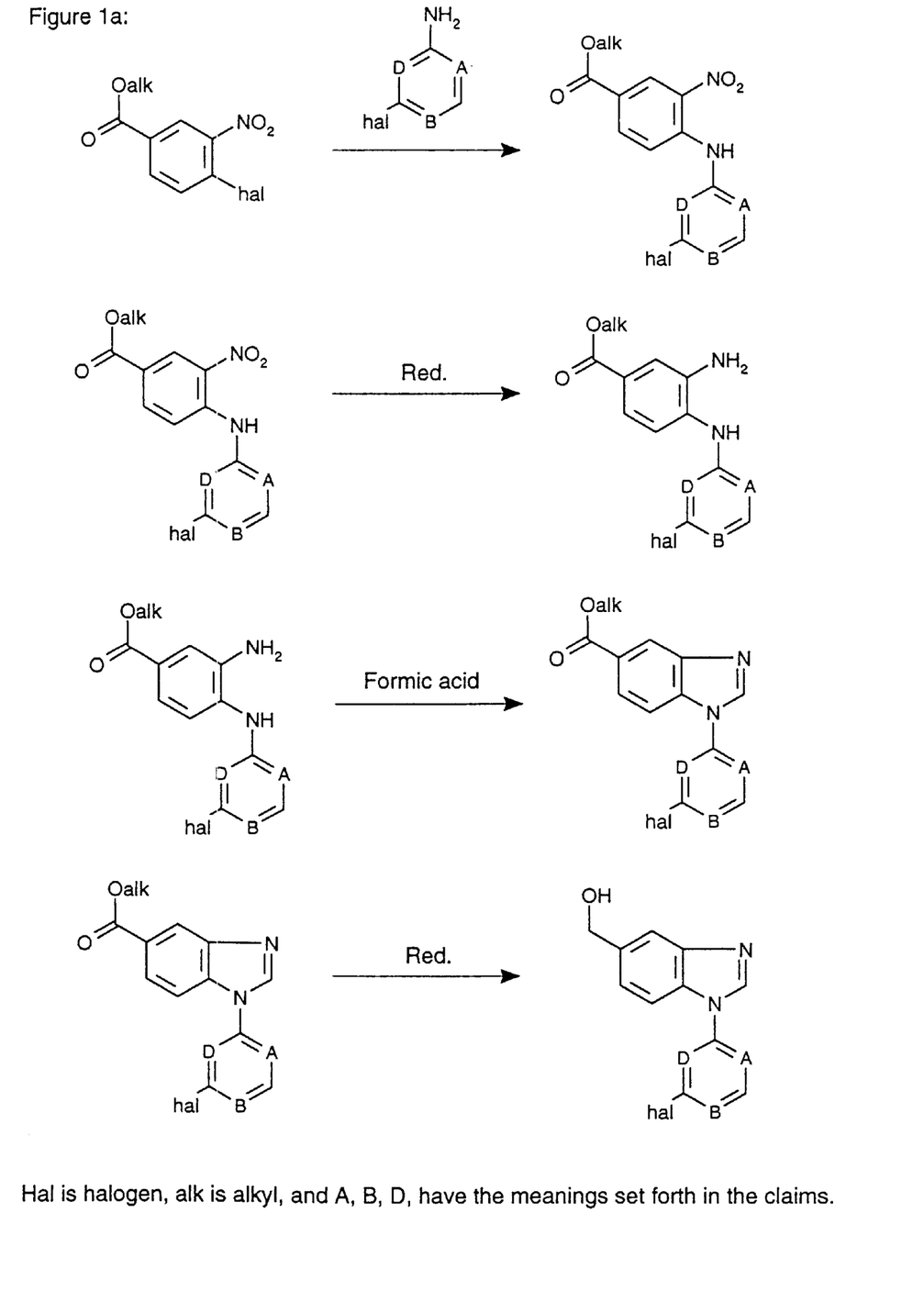
FIGS. 1a, 1b, 2, 3, and 4 describe methods for the preparation of compounds of the invention wherein $R^6$ is an oxime and $R^7$ is hydrogen. Compounds of the invention wherein $R^7$ is oxime and $R^6$ is hydrogen can be synthesized analogously.
Figure 1B:
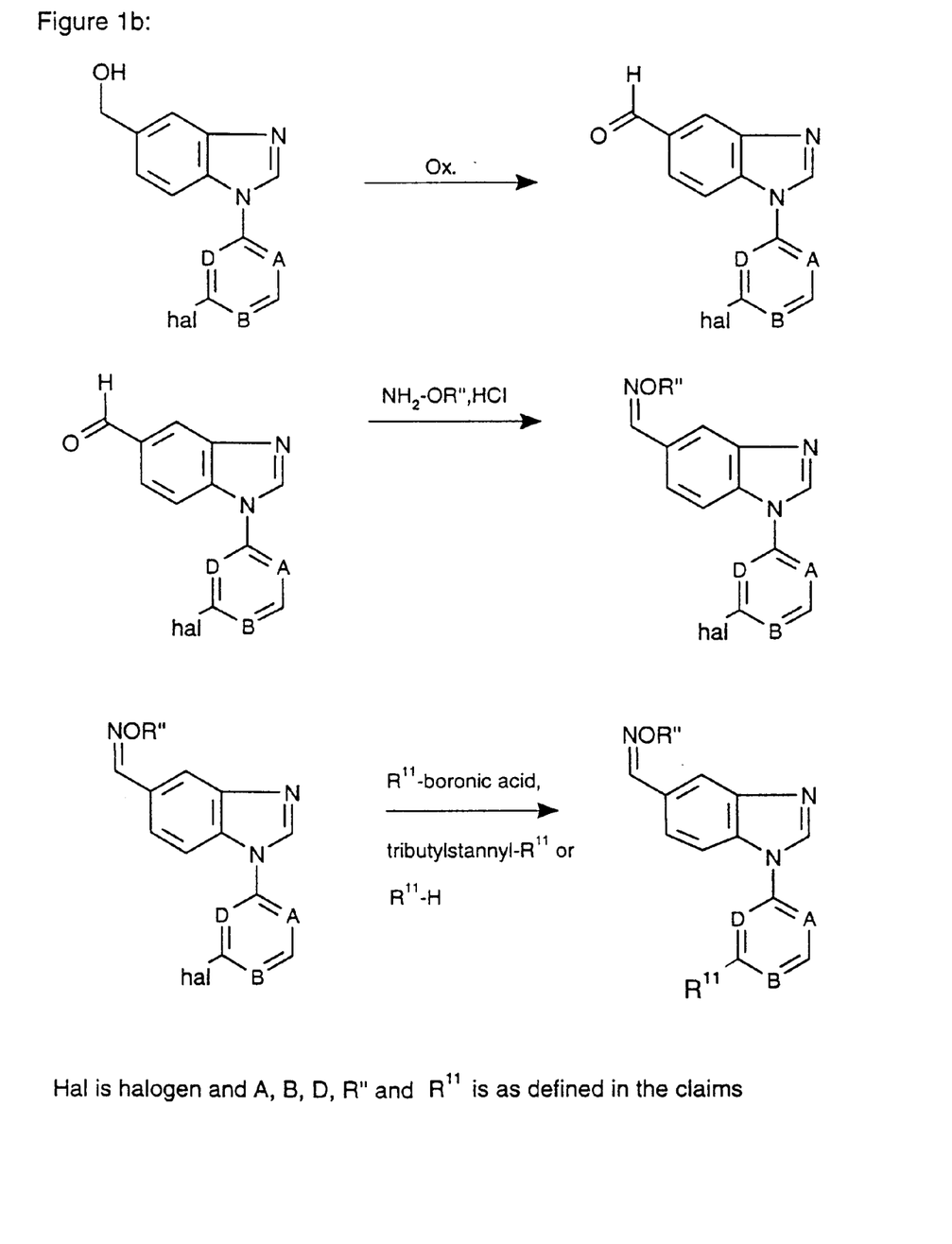
Figure 2:
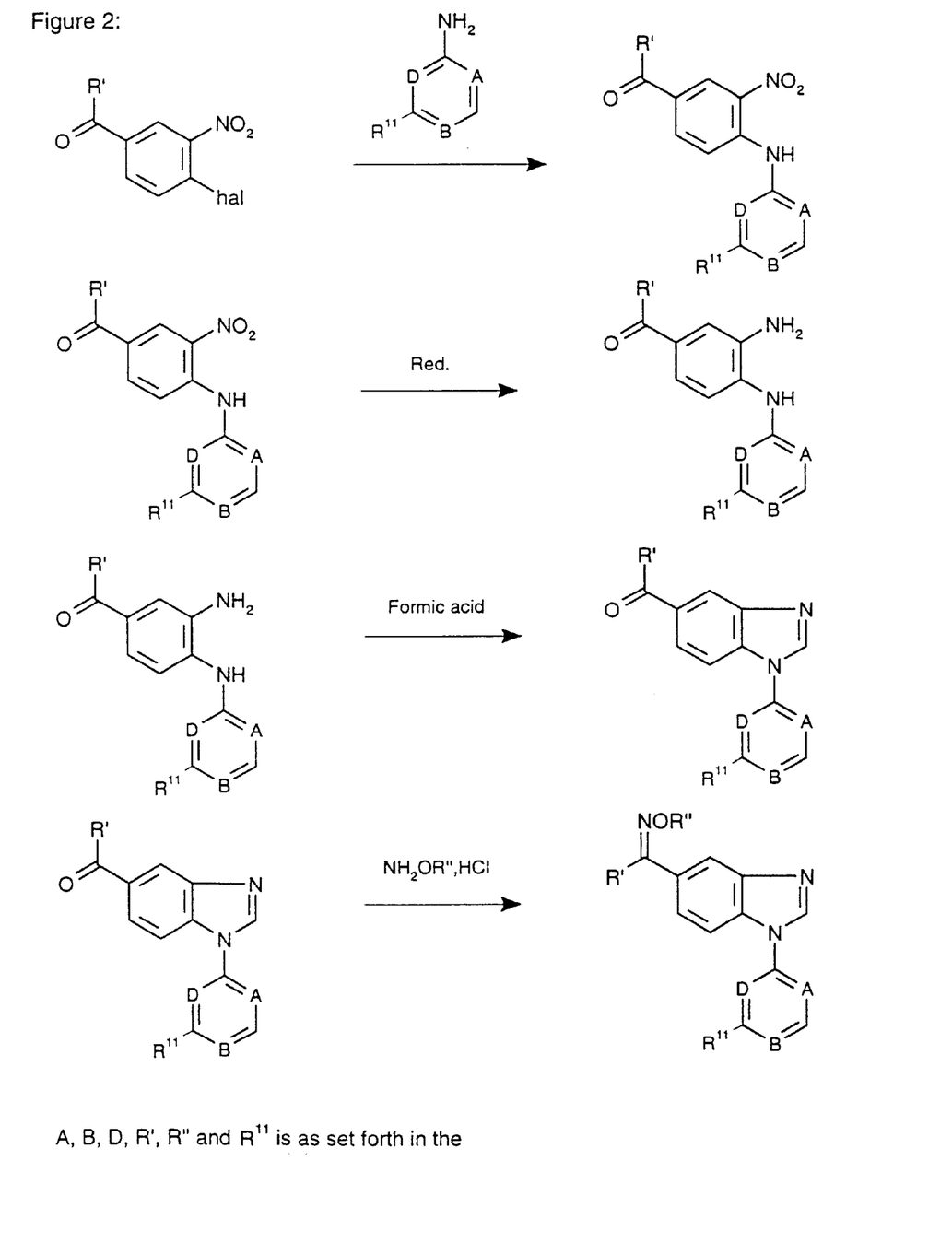
Figure 3:
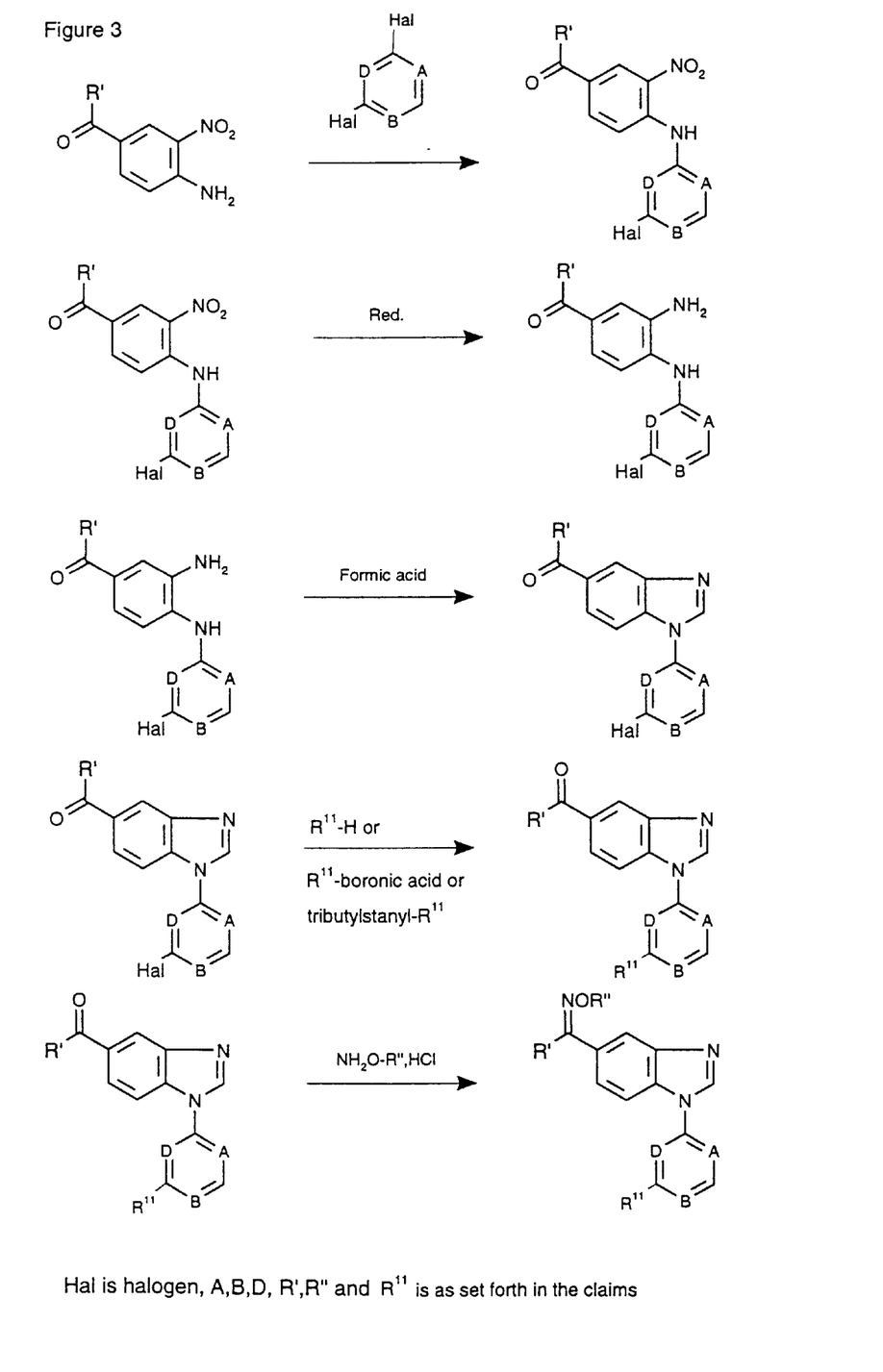
Figure 4:
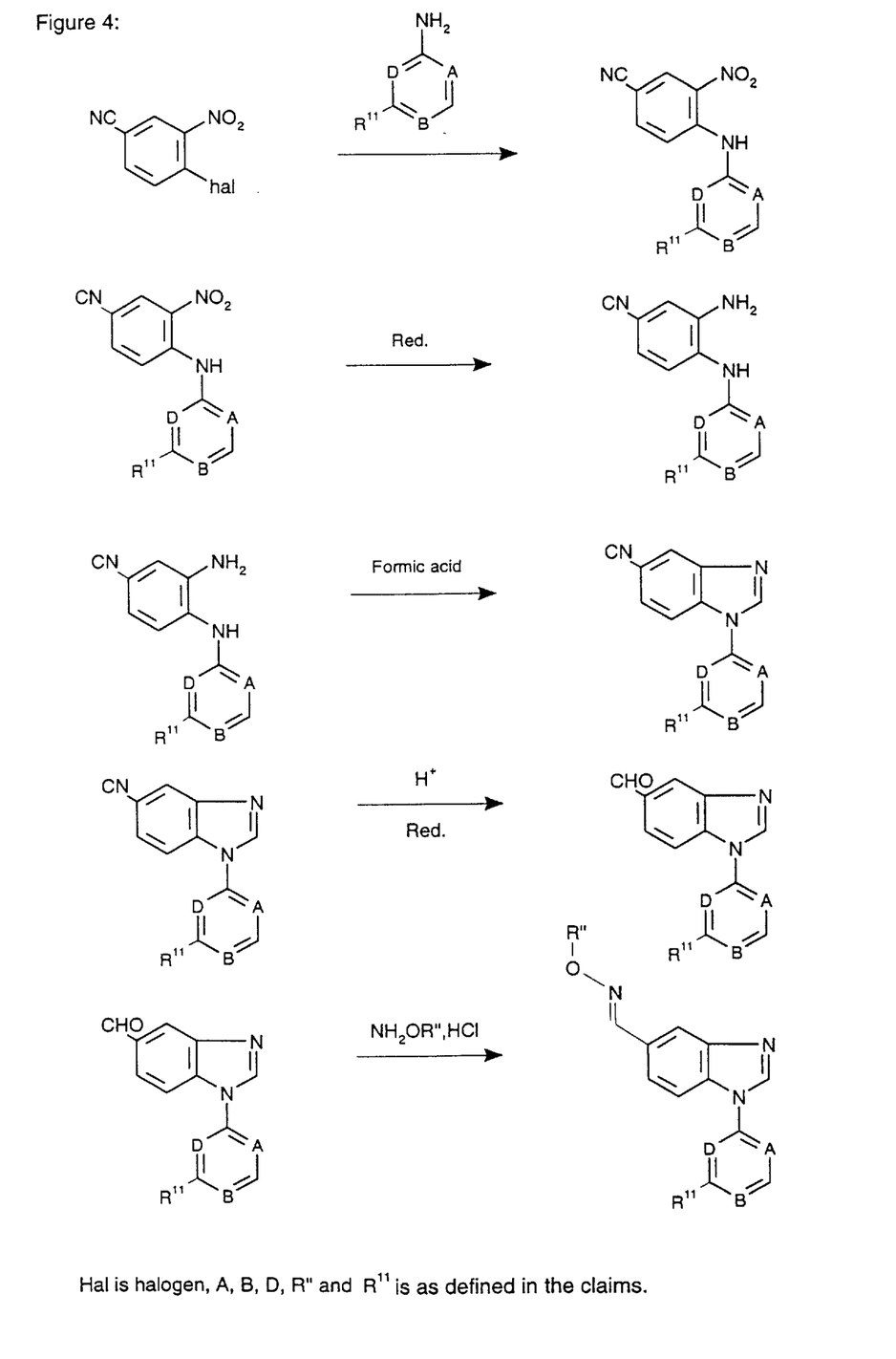

Starting materials for the processes described in the present patent application are known or can be prepared by known processes from commercially available chemicals.

The products of the reactions described herein are isolated by conventional means such as extraction, crystallization, distillation, chromatography, and the like.

Biology 4-aminobytyric acid (GABA) is the major inhibitory neurotransmitter and has been shown to act throughout both the central and peripheral nervous system. At present two types of GABA receptors are known, the $GABA_A$ and the $GABA_B$ receptors. Recent molecular biology has demonstrated that the $GABA_A$ receptors can be subdivided into numerous subreceptors consistant with the selective and or partial pharmacological effects observed with certain benzodiazepine receptor ligands as opposed to the unselective effects observed for the classical benzodiazepine receptor ligands such as for example diazepam. Activation of GABA receptors leads to alternations in membrane potential (hyperpolarization). The $GABA_A$ receptors are associated with chloride influx through its associated and integrated chloride channel, whereas $GABA_B$ receptor activation indirectly alters potassium and calcium channels as well as modifies second messenger production. The $GABA_A$ recognition sites can be activated by GABA, muscimol; and isoguvacine for example, but not by $GABA_B$ agonists such as for example baclofen. The modulatory $GABA_A$ recognition site at the benzodiazepine receptor sites can be selectively radiolabelled with $^3$H-flunitrazepam. The affinity of various potential ligands for the benzodiazepine receptor sites can thus be evaluated by estimating the ability of test compounds to displace $^3$H-flunitrazepam.

Method

Tissue Preparation: Preparations are performed at 0–4° C. unless otherwise indicated. Cerebral cortex from male Wistar rats (150–200 g) is homogenized for 5–10 sec in 20 ml Tris-HCl (30 mM, pH 7.4) using an Ultra-Turrax homogenizer. The suspension is centrifuged at 27,000×g for 15 min and the pellet is washed three times with buffer (centrifuged at 27,000×g for 10 min). The washed pellet is homogenized in 20 ml of buffer and incubated on a water bath (37° C.) for 30 min to remove endogenous GABA and then centrifuged for 10 min at 27,000×g. The pellet is then homogenized in buffer and centrifuged for 10 min at 27,000×g. The final pellet is resuspended in 30 ml buffer and the preparation is frozen and stored at –20° C.

Assay: The membrane preparation is thawed and centrifuged at 2° C. for 10 min at 27,000×g. The pellet is washed twice with 20 ml 50 mM Tris-citrate, pH 7.1 using an Ultra-Turrax homogenizer and centrifuged for 10 min at 27,000×g. The final pellet is resuspended in 50 mM Tris-citrate, pH 7.1 (500 ml buffer per g of original tissue), and then used for binding assays. Aliquots of 0.5 ml tissue are added to 25 µl of test solution and 25 µl of $^3$H-FNM (1 nM, final concentration), mixed and incubated for 40 min at 2° C. Non-specific binding is determined using clonazepam (1 µM, final concentration). After incubation the samples are added 5 ml of ice-cold buffer and poured directly onto Whatman GF/C glass fibre filters under suction and immediately washed with 5 ml ice-cold buffer. The amount of radioactivity on the filters is determined by conventional liquid scintillation counting. Specific binding is total binding minus non-specific binding.

The test value is calculated as the $IC_{50}$ (the concentration (nM) of the test substance which inhibits the specific binding of $^3$H-FNM by 50%).

Test results obtained by testing selected compounds of the present invention appear from the following table:

TABLE

| Test compound: | $IC_{50}$(nM) |
|---|---|
| 1-(3-(3-furanyl)-phenyl)-5-formyl-benzimidazole O-methyl oxime | 1.5 |
| 5-acetyl-1-(3-(3-pyridyl)-phenyl)-benzimidazole O-ethyl oxime | 1.4 |
| 5-acetyl-1-(3-(1-imidazolyl)-phenyl)-benzimidazole O-methyl oxime | 0.6 |
| 5-acetyl-1-(3-(1-imidazolyl)-phenyl)-benzimidazole O-ethyl oxime | 1.2 |
| 5-acetyl-1-(3-(2-thiazolyl)-phenyl)-benzimidazole O-methyl oxime | 1.7 |

Pharmaceutical Compositions

While it is possible that, for use in therapy, a compound of the invention may be administered as the raw chemical, then it is preferable to present the active ingredient as a pharmaceutical formulation.

The invention thus further provides a pharmaceutical formulation comprising a compound of the invention or a pharmaceutically acceptable salt or derivative thereof together with one or more pharmaceutically acceptable carriers therefor and, optionally, other therapeutic and/or prophylactic ingredients. The carrier(s) must be "acceptable" in the sense of being compatible with the other ingredients of the formulation and not deleterious to the recipient thereof.

Pharmaceutical formulations include those suitable for oral, rectal, nasal, topical (including buccal and sub-lingual), vaginal or parenteral (including intramuscular, subcutaneous and intravenous) administration or in a form suitable for administration by inhalation or insufflation.

The compounds of the invention, together with a conventional adjuvant, carrier, or diluent, may thus be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, in the form of suppositories for rectal administration; or in the form of sterile injectable solutions for parenteral (including subcutaneous) use. Such pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed. Formulations containing one (1) milligram of active ingredient or, more broadly, 0.01 to one hundred (100) milligrams, per tablet, are accordingly suitable representative unit dosage forms.

The compounds of the present invention can be administrated in a wide variety of oral and parenteral dosage forms. It will be obvious to those skilled in the art that the following dosage forms may comprise as the active component, either a compound of the invention or a pharmaceutically acceptable salt of a compound of the invention.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavouring agents, solubilizers, lubricants, suspending agents, binders, preservatives, tablet disintegrating agents, or an encapsulating material.

In powders, the carrier is a finely divided solid which is in a mixture with the finely divided active component.

In tablets, the active component is mixed with the carrier having the necessary binding capacity in suitable proportions and compacted in the shape and size desired.

The powders and tablets preferably contain from one to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting vax, cocoa butter, and the like. The term "preparation" is intended to include the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets, and lozenges can be used as solid forms suitable for oral administration.

For preparing suppositories, a low melting vax, such as a mixture of fatty acid glycerides or cocoa butter, is first melted and the active component is dispersed homogeneously therein, as by stirring. The molten homogenous mixture is then poured into convenient sized molds, allowed to cool, and thereby to solidify.

Formulations suitable for vaginal administration may be presented as pessaries, tampons, creams, gels, pastes, foams or sprays containing in addition to the active ingredient such carriers as are known in the art to be appropriate.

Liquid form preparations include solutions, suspensions, and emulsions, for example, water or water propylene glycol solutions. For example, parenteral injection liquid preparations can be formulated in solutions in aqueous polyethylene glycol solution.

The compounds according to the present invention may thus be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulatory agents such as suspending, stabilising and/or dispersing agents. Alternatively, the active ingredient may be in powder form, obtained by aseptic isolation of sterile solid or by lyophilisation from solution, for constitution with a suitable vehicle, e.g. sterile, pyrogen-free water, before use.

Aqueous solutions suitable for oral use can be prepared by dissolving the active component in water and adding suitable colorants, flavours, stabilizing and thickening agents, as desired.

Aqueous suspensions suitable for oral use can be made by dispersing the finely divided active component in water with viscous material, such as natural or synthetic gums, resins, methylcellulose, sodium carboxymethylcellulose, and other well known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavours, stabilizers, buffers, artificial and natural sweeteners, dispersants, thickeners, solubilizing agents, and the like.

For topical administration to the epidermis the compounds according to the invention may be formulated as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also contain one or more emulsifying agents, stabilising agents, dispersing agents, suspending agents, thickening agents, or colouring agents.

Formulations suitable for topical administration in the mouth include lozenges comprising active agent in a flavoured base, usually sucrose and acacia or tragacanth; pastilles comprising the active ingredient in an inert base such as gelatin and glycerin or sucrose and acacia; and mouthwashes comprising the active ingredient in a suitable liquid carrier.

Solutions or suspensions are applied directly to the nasel cavity by conventional means, for example with a dropper, pipette or spray. The formulations may be provided in single or multidose form. In the latter case of a dropper or pipette this may be achieved by the patient administering an appropriate, predetermined volume of the solution or suspension. In the case of a spray this may be achieved for example by means of a metering atomising spray pump.

Administration to the respiratory tract may also be achieved by means of an aerosol formulation in which the active ingredient is provided in a pressurised pack with a suitable propellant such as a chlorofluorocarbon (CFC) for example dichlorodifluoromethane, trichlorofluoromethane, or dichlorotetrafluoroethane, carbon dioxide or other suitable gas. The aerosol may conveniently also contain a surfactant such as lecithin. The dose of drug may be controlled by provision of a metered valve.

Alternatively the active ingredients may be provided in the form of a dry powder, for example a powder mix of the compound in a suitable powder base such as lactose, starch, starch derivatives such as hydroxypropylmethyl cellulose and polyvinylpyrrolidine (PVP). Conveniently the powder carrier will form a gel in the nasal cavity. The powder composition may be presented in unit dose form for example in capsules or cartridges of e.g. gelatin or blister packs from which the powder may be administered by means of an inhaler.

In formulations intended for administration to the respiratory tract, including intranasal formulations, the compound will generally have a small particle size for example of the order of 5 microns or less. Such a particle size may be obtained by means known in the art, for example by micronization.

When desired, formulations adapted to give sustained release of the active ingredient may be employed.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Tablets or capsules for oral administration and liquids for intravenous administration are preferred compositions.

Method of Treating

The compounds of this invention are extremely useful in the treatment of disorders or diseases of a living animal body due to their affinity for the benzodiazepine binding site of the $GABA_A$ receptor. These properties make the compounds of this invention extremely useful in the treatment of convulsions, anxiety, sleep disorders, memory disorders as well as other disorders sensitive to modulation of the $GABA_A$ receptor. The compounds of this invention may accordingly be administered to a subject, including a human, in need of treatment, alleviation, or elimination of a disorder or disease associated with the $GABA_A$ receptors. This includes especially convulsions, anxiety, sleep disorders and memory disorders.

Suitable dosage range are 0.01–100 milligrams daily, 0.1–50 milligrams daily, and especially 0.1–30 milligrams daily, dependent as usual upon the exact mode of administration, form in which administered, the indication towards which the administration is directed, the subject involved and the body weight of the subject involved, and further the preference and experience of the physician or veterinarian in charge.

The following examples will illustrate the invention further; however they are not to be construed as limiting. The compounds of the invention prepared in the following examples are listed in table 1 on pages 30–31.

EXAMPLE 1

4-Fluoro-3-nitroacetophenone (1 g): Concentrated sulfuric acid (200 ml) is cooled to 5° C. 4-Fluoroacetophenone (20 ml, 0.16 mol) is added keeping the temperature below 10° C. The mixture is cooled to 0–5° C. and potassium nitrate (25 g, 0.25 mol) is added portionwise over 2 hours keeping the temperature within this range. Following the addition the mixture is stirred in the cold for additionally 2 hours. The mixture is poured on ice (600 g) and the crude product is filtered off. Column-chromatographic purification on silica gel using a mixture of ethyl acetate and petroleum ether (1:9) as the eluent affords pure 1 g (18.2 g, 60%). Mp 48–49° C.

4-Amino-3-nitroacetophenone (1 h): A suspension of 4-aminoacetophenone (25 g, 184 mmol) in 250 ml acetic anhydride is stirred at ambient temperature for 30 min. The mixture is cooled to 0° C. and conc. nitric acid (18 ml) is added dropwise, keeping the temperature at −5–5° C. Following the addition the mixture is allowed to warm to room temperature and stirring is continued at ambient temperature over night. The mixture is poured into ice-water (700 ml) and the product: N-(4-acetyl-2-nitrophenyl)acetamide is filtered off, washed thoroughly with water and dried. Yield: 26.5 g (65%). This product was added to a hot mixture of water (50ml) and conc. sulfuric acid (100 ml) and the resulting mixture was stirred for 15 min. 1 h precipitates from the cooled mixture upon dilution with water. The product is filtered off, washed with water and dried. Yield: 91%. Mp 121–123° C.

EXAMPLE 2

3-(3-Pyridyl)aniline (2a): A mixture of diethyl 3-pyridylborane (16.3 g, 0.11 mol), 3-bromoaniline (12.2 ml, 0.11 mol), potassium carbonate (45.8 g, 0.33 mol) and tetrakis(triphenylphosphine)palladium(0) (80 mg) in a mixture of water (40 ml) and dimethoxyethane (80 ml) is heated to 80° C. under a stream of nitrogen over night. After cooling the mixture is diluted with water and ethyl acetate and filtered through a fluted filterpaper. The layers are separated. The aqueous layer is extracted once with ethyl acetate. The combined organic phases are dried over sodium sulfate and concentrated under reduced pressure. The residue is dissolved in ethanol. Water is added and the mixture is evaporated to dryness. This residue crystallizes upon trituration with ice-cold water. The crystals are collected, dried and washed with petroleum ether to afford pure 2a (16.3 g, 87%). Mp 75–76° C.

3-(5-Pyrimidyl)aniline (2b): A suspension of 5-bromopyrimidine (15 g, 94.3 mmol), 3-aminophenylboronic acid hemisulfate (19.3 g, 104 mmol), sodium bicarbonate (39.6 g, 472 mmol) and tetrakis (triphenylphosphine)palladium(0) (1 g) in a mixture of water (75 ml) and dimethoxyethane (150 ml) is heated to 80° C. under a stream of nitrogen over night. After cooling the mixture is poured into ice-water. The precipitate is filtered off, washed with water and dried to yield 2b (15 g, 93%). Mp 164–165° C.

3-(1-Imidazolyl)aniline (2d): A mixture of 1-iodo-3-nitrobenzene (90 g, 0.36 mol), imidazole (54 g, 0.79 mol), potassium carbonate (54 g, 0.39 mol) and finely divided copper powder (1 g) is heated to 200° C. The melt is stirred for 2 hours under nitrogen. During the reaction water vapor is trapped by molecular sieves, placed between the reation vessel and the condenser. Following the reaction the mixture is cooled to 100° C. and water is added. The mixture is allowed to cool to room temperature and the crude product is filtered off and dried. Recrystallization from toluene (200–250 ml) affords pure 3-(1-imidazolyl)nitrobenzene (54.2 g, 79%). Mp 101–102° C.

To 3-(1-imidazolyl)nitrobenzene (51.6 g, 0.27 mol) in acetic acid (500 ml) is added palladium catalyst (5 g 5% Pd on activated carbon) and the mixture is hydrogenated under pressure ($P_{start}$:4 bar) until the hydrogen uptake has ceased. The mixture is filtered through celite and the filtrate is evaporated to dryness to leave 2d as a light-brown oil. Yield: 40.4 g (93%).

N-Acetyl 3-(1-imidazolyl)aniline (2e): 2d (5.88 g, 37 mmol) is stirred in acetic anhydride (30 ml) at ambient temperature for 1 hour. The mixture is poured into ice-water and rendered alkaline by addition of aqueous sodium hydroxide (12M). The product is filtered off, washed with water and dried to yield 2e (6.34 g, 85%). Mp 181–183° C.

3-(2-Pyridyl)aniline (2f): To a solution of 2-(3-nitrophenyl)pyridine (prepared as described in J. Chem. Soc. 1958 p. 1759) (12.7 g, 63.5 mmol) in abs. ethanol is added palladium catalyst (1.3 g 5% Pd on activated carbon) and the mixture is hydrogenated at ambient pressure until the hydrogen uptake has ceased. The mixture is filtered through celite and the filtrate is concentrated under reduced pressure. The residue is purified by column-chromatography on silica gel using a mixture of ethyl acetate and petroleum ether (9:1) as the eluent to afford 2f (9.5 g, 88%) as a light brown oil.

3-(2-Aminopyrimid-5-yl)aniline (2l): A mixture of 2-(acetamino)-5-bromopyrimidine (5.4 g, 25 mmol), 3-aminophenylboronic acid hemisulfate (5.58 g, 30 mmol), potassium carbonate (10.4 g, 75 mmol), 1,3-propanediol (9 ml, 0.13 mmol) and tetrakis(triphenylphosphine)palladium (0) (0.5 g) in a mixture of water (25 ml) and dimethoxyethane (50 ml) is stirred at 80° C. under a stream of nitrogen over night. After cooling the mixture is poured into ice-water. The product (deacetylated during the reaction) is filtered off, washed with water and dried to yield 2l (4.19 g, 90%). Mp 171–172° C.

EXAMPLE 3 i-Propyl 4-(3-bromophenyl)amino-3-nitrobenzoate (24): A mixture of i-propyl 4-chloro-3-nitrobenzoate (25.88 g, 0.11 mol), 3-bromoaniline (17.36 ml, 0.16 mol) and potassium carbonate (14.63 g, 0.11 mol) in N-methyl-2-pyrrolidone (25 ml) is heated to 150° C. for 3 days. After cooling the mixture is poured into diluted hydrochloric acid (300 ml, 1 M). The precipitate is filtered off, washed with water and dried (37.4 g). This crude product is washed with hot 2-propanol to afford pure 24 (26.25 g, 65%). Mp 162–165° C.

EXAMPLE 4 i-Propyl 3-amino-4-(3-bromophenyl)aminobenzoate (25): 24 from Example 3 (3.79 g, 10 mmol) is suspended in a mixture of ethanol (30 ml) and dichloromethane (30 ml). Wet Raney nickel (0.5 g) is added and the mixture is hydrogenated until the hydrogen uptake has ceased. The mixture is filtered through celite and the solvent is removed under reduced pressure to leave 25 quantitatively. Mp 82–85° C.

5-Acetyl-2-((3-bromophenyl)amino)aniline in mixture with 5-Acetyl-2-((3-iodophenyl)amino)aniline (35) was prepared analogously from 34 (Example 16). The product was isolated as an oil.

EXAMPLE 5

5-Acetyl-1-(3-(3-pyridyl)phenyl)benzimidazole (32a): A solution of 31a from Example 13 (7 g, 23.1 mmol) in formic acid (20 ml) is stirred overnight at ambient temperature. The mixture is poured into water (750 ml) and rendered basic with concentrated aqueous ammonia. The precipitate is filtered off, washed with water and dried. The crude product is dissolved in refluxing ethanol. Water is added until onset of precipitation. The mixture is allowed to cool. The product is filtered off and dried to yield 4.3 (60%). Mp. 200–202° C.

1-(3-Bromophenyl)-5-(i-propylcarboxy)benzimidazole (26) was prepared analogously from 25 (Example 4). Yield: 85%. Mp 102–104° C.

5-Acetyl-1-(3-iodophenyl)benzimidazole in mixture with 5-acetyl-(3-bromophenyl)benzimidazole (36) was prepared analogously from 35 (Example 4). Yield: ~91% (2 steps from 34).

5-Acetyl-1-(3-(5-pyrimidyl)phenyl)benzimidazole (32b) was prepared analogously from 31b (Example 13).Yield: 71%. Mp 253–254° C.

5-Acetyl-1-(3-(2-pyridyl)phenyl)benzimidazole (32c) was prepared analogously from 31c (Example 13). Yield: 91%. Mp 158–159° C.

5-Acetyl-1-(3-(2-aminopyrimid-5-yl)phenyl) benzimidazole (32d) was prepared analogously from 31d (Example 13). Yield: 84%. Mp 275–278° C.

EXAMPLE 6

1-(3-Bromophenyl)-5-(hydroxymethyl)benzimidazole (27): A stirred suspension of 26 from Example 5 (18 g, 50.18 mmol) in 300 ml dry diethyl ether is kept under a stream of nitrogen at room temperature. LiAlH$_4$ (1.9 g, 50 mmol) is added in portions and the mixture is stirred over night. The mixture is poured into a mixture of ice-water and ethyl acetate. The resulting emulgation is filtered through celite and the phases are separated. The aqueous phase is extracted once with ethyl acetate. The combined organic phases are washed with water, dried over sodium sulfate and concentrated under reduced pressure. The residue is chromatographied on silica gel using successively ethyl acetate and a mixture of ethyl acetate and methanol (9:1) as eluents. Yield of 27: 7.69 g (51%). Mp 107–109° C.

EXAMPLE 7

1-(3-Bromophenyl)-5-formylbenzimidazole (28): A mixture of 27 from Example 6 (3.9 g, 12.9 mmol) and benzeneseleninic acid (3.04 g, 16.1 mmol) in toluene is stirred at 70° C. over night. The product precipitates upon cooling. The precipitate is filtered off, washed with petroleum ether and dried. Subsequent washings with aqueous sodium carbonate and water affords pure 28. Yield: 2.99 g (77%). Mp 179–181° C.

EXAMPLE 8

1-(3-Bromophenyl)-5-formylbenzimidazole O-methyl oxime (29a): To a suspension of 28 from Example 7 (2.95 g, 9.8 mmol) in abs. ethanol (100 ml) is added methoxylamine hydrochloride (1.23 g, 14.7 mmol) and the mixture is heated to 70° C. Sodium bicarbonate (1.23 g, 14.7 mmol) is added in portions over 20 min. Following the addition the mixture is stirred at 70° C. for additionally 2 hours. After cooling the solvent is removed under reduced pressure. Water is added to the residue and the product is filtered off, washed with water and dried. Yield: 2.77 g (86%). Mp 119–120° C.

EXAMPLE 9

1-(3-(2-Thienyl)phenyl)-5-formylbenzimidazole O-methyl oxime (29d): A mixture of 29a from Example 8 (0.7 g, 2.1 mmol), 2-(tributylstannyl)thiophene (1.59 g, 4.3 mmol) and tris(triphenylphosphine)palladium dichloride (50 mg) in DMF (5 ml) is heated to 80° C. over night. The cooled reaction mixture is diluted with 4 volumes of water and extracted with ethyl acetate. The combined organic extracts are dried over sodium sulfate and concentrated under reduced pressure. The residue is purified by columnchromatography on silica gel using a mixture of ethyl acetate and petroleum ether (1:1) as the eluent. Yield: 0.56 g (80%). Mp 184–185° C.

EXAMPLE 10

1-(3-(3-Furanyl)phenyl)-5-formylbenzimidazole O-methyl oxime (29c): A mixture of 1-(3-Bromophenyl)-5-formylbenzimidazole O-methyloxime (29a) from Example 8 (0.7 g, 2.1 mmol), 3-furanylboronic acid (0.26 g, 2.34 mmol), sodium bicarbonate (0.89 g, 10.6 mmol) and tetrakis (triphenylphosphine)palladium(0) (50 mg) in a mixture of water (5 ml) and dimethoxyethane (10 ml) is stirred at 80° C. under nitrogen over night. After cooling water is added and the mixture is extracted with ethyl acetate. The extract is dried over sodium sulfate and concentrated under reduced pressure. The residue is eluted through silica gel with a mixture of ethyl acetate and petroleum ether (1:1). The pure fractions are evaporated to dryness. Trituration with petroleum ether affords a white, crystalline product. Yield: 0.42 g (63%). Mp 147–148° C.

EXAMPLE 11

1-(3-(1-Imidazolyl)phenyl)-5-formylbenzimidazole O-methyl oxime (29b): A mixture of 1-(3-bromophenyl)-5-formylbenzimidazol O-methyloxime (29a) from Example 8 (0.7 g, 2.13 mmol), imidazole (0.33 g, 4.85 mmol), potassium carbonate (0.29 g, 2.13 mmol) and a catalytic amount of copper-bronze in 5 ml N-methyl-2-pyrrolidone is heated to 140° C. under a stream of nitrogen for 24 hours. After cooling the mixture is poured into water. A small volume of methanol is added and the mixture is extracted with dichloromethane. The extract is dried over sodium sulfate and concentrated under reduced pressure. The residue is eluted through silica gel with a mixture of dichloromethane and ethanol (10:1) to yield pure 29b. Yield: 0.23 g (34%) Mp. 197–199° C.

5-Acetyl-1-(3-(1-imidazolyl)phenyl)benzimidazole (37) was prepared analogously from 36 (Example 5). Yield: ~26%. Mp 205–206° C.

EXAMPLE 12

5-Acetyl-2-nitro-N-(3-(3-pyridyl)phenyl)aniline (30a): A mixture of 1 g from Example 1 (5 g, 27.3 mmol) and 2a from Example 2 (4.62 g, 27.2 mmol) in dry N-methyl-2-pyrrolidone (10 ml ) is stirred at 40–50° C. over night. The resulting solid reaction mixture is suspended in ice-water and rendered alkaline by addition of aqueous sodium carbonate (1 M). The product is filtered off, washed with water and dried to yield 7.68 g 30a (85%). Mp 112–113° C.

4-Acetyl-2-nitro-N-(3-(5-pyrimidyl)phenyl)aniline (30b) was prepared analogously from 1 g (Example 1) and 2b (Example 2). Yield: 65%. Mp 131–132° C.

4-Acetyl-2-nitro-N-(3-(2-pyridyl)phenyl)aniline (30c) was prepared analogously from 1 g (Example 1) and 2f (Example 2). Yield: 87%. Mp 195–196° C.

4-Acetyl-2-nitro-N-(3-(2-aminopyrimid-5-yl)phenyl) aniline (30d) was prepared analogously from 1 g (Example 1) and 21 (Example 2). Yield: 80%. Mp 233–236° C.

EXAMPLE 13

5-Acetyl-2-(3-(3-pyridyl)phenylamino)aniline (31a): 30a from Example 12 (2 g, 6 mmol) is suspended in a mixture of ethanol (50 ml) and dichloromethane (10 ml) and is hydrogenated at ambient pressure using palladium (5% on activated carbon) as the catalyst. Filtration of the resulting solution through celite followed by evaporation of solvent leaves an oil. Trituration with a mixture of diethyl ether and petroleum ether (1:1) affords 1.46 g pure 31a (80%). Mp 175–176° C.

5-Acetyl-2-(3-(5-pyrimidyl)phenylamino)aniline (31b) was prepared analogously from 30b (Example 12) The crude oily product was used for the next step (Example 5) without purification.

5-Acetyl-2-(3-(2-pyridyl)phenylamino)aniline (31c) was prepared analogously from 30c (Example 12). Yield: 92%. Mp 145–146° C.

5-Acetyl-2-(3-(2-aminopyrimid-5-yl)phenylamino) aniline (31d) was prepared analogously from 30d (Example 12). Yield: 71%. Mp 228–230° C.

EXAMPLE 14

5-Acetyl-1-(3-(3-pyridyl)phenyl)benzimidazole O-ethyl oxime (33a): 32a from Example 5 (5 g, 15.97 mmol) is suspended in absolute ethanol (50 ml) and heated to 70° C. O-Ethyl hydroxylamine hydrochloride (2.4 g, 24.61 mmol) is added and the mixture is heated to reflux for 1.5 hours. After cooling the solvent is removed by evaporation, and the residue is stirred with aqueous sodium hydroxide (50 ml, 1 M). The crude product is filtered off. Column-chromatographic workup on silica gel using a mixture of ethyl acetate and ethanol (9:1) as the eluent affords pure 33a. Yield: 3.7 g (65%). Mp 105–106° C.

The following compounds were prepared analogously from 32a (Example 5) and the appropriate O-alkyl-, O-alkenyl-, and O-alkynyl hydroxylamine hydrochlorides:

5-Acetyl-1-(3-(3-pyridyl)phenyl)benzimidazole O-propargyl oxime (33b). Yield: 49%. Mp 138–140° C.

5-Acetyl-1-(3-(3-pyridyl)phenyl)benzimidazole O-allyl oxime (33c). Yield: 73%. Mp 87–89° C.

5-Acetyl-1-(3-(3-pyridyl)phenyl)benzimidazole O-iso-butyl oxime (33f). Yield: 38%. Mp 90–92° C.

5-Acetyl-1-(3-(3-pyridyl)phenyl)benzimidazole O-methyl oxime (33g). Yield: 59%. Mp 145–146° C.

5-Acetyl-1-(3-(3-pyridyl)phenyl)benzimidazole oxime (33i). Yield: 82%. Mp 218–220° C.

The following compounds were prepared analogously from the appropriate O-alkyl hydroxylamine hydrochlorides and 32b, 32c and 32d (Example 5) respectively:

5-Acetyl-1-(3-(5-pyrimidyl)phenyl)benzimidazole O-ethyl oxime (33d). Yield: 54%. Mp 187–188° C.

5-Acetyl-1-(3-(2-pyridyl)phenyl)benzimidazole O-ethyl oxime (33e). Yield: 53%. Mp 107–108° C.

5-Acetyl-1-(3-(2-aminopyrimid-5-yl)phenyl) benzimidazole O-methyl oxime (33h). Yield: 62%. Mp 236–238° C.

The following compounds were prepared analogously from 37 (Example 11) and O-methyl hydroxylamine hydrochloride and O-ethyl hydroxylamine hydrochloride, respectively:

5-Acetyl-1-(3-(1-imidazolyl)phenyl)benzimidazole O-methyl oxime (38a). Yield: 67%. Mp 230–231° C.

5-Acetyl-1-(3-(1-imidazolyl)phenyl)benzimidazole O-ethyl oxime (38b). Yield: 67%. Mp 135–138° C.

EXAMPLE 15

5-Acetyl-1-(3-(3-pyridyl)phenyl)benzimidazole O-iso-propyl oxime (33j): To a suspension of 33i (Example 14) (0.4 g, 1.22 mmol) in dry DMF (5 ml) is added sodium hydride (50 mg of a 60% dispersion in mineral oil). The mixture is stirred at 30–40° C. for 30 min. 2-Bromopropane (0.14 ml, 1.49 mmol) is added and the mixture is stirred at 40° C. over night. After cooling the mixture is diluted with 4 volumes of water and extracted with dichloromethane. The organic extract is concentrated and eluted through silica gel with ethyl acetate to yield 0.15 g 33j (33%). Mp 77–80° C.

EXAMPLE 16

4-Acetyl-N-(3-bromophenyl)-2-nitroaniline in mixture with 4-acetyl-N-(3-iodophenyl)-2-nitroaniline (34): A mixture of 4-acetyl-2-nitroaniline (1 h) from Example 1 (15.6 g, 86.7 mmol), 3-bromo-1-iodobenzen (13.3 ml, 104 mmol), potassium carbonate (12 g, 87 mmol) and catalytic amounts of cupous iodide and copper-bronze is heated with stirring to 180° C. under a stream of nitrogen for 24 hours. The mixture is allowed to cool to 70° C. and the tarry reaction cake is extracted twice with hot ethyl acetate. The combined extracts are purified by coloumn-chromatography on silica gel using a mixture of ethylacetate and petroleum ether (3:7) as the eluent to yield 9 g product mixture.

EXAMPLE 17

2-(Tributylstannyl)thiazole (50): To a solution of thiazole (0.71 ml, 10 mmol) in dry THF (20 ml) was added dropwise 1.6 M-BuLi in hexane (6.9 ml, 11 mmol) under argon at −78° C. The reaction mixture was stirred at −78° C. for 0.5 hr and Bu$_3$SnCl (3.1 ml, 11 mmol) was added dropwise. After stirring for 1 hr at −78° C. and for 1 hr at room temperature, the mixture was concentrated, triturated with water (50 ml) and extracted with diethylether (100 ml×3). The extract was washed with brine, dried and concentrated under reduced pressure to give (50) as a colorless oil. (3.7 g, quant.).

EXAMPLE 18

5-Acetyl-1-(3-(2-thiazolyl)phenyl)benzimidazole (51): To a solution of (50) from Example 17 (3.6 g, 9.7 mmol) in dry THF (20 ml) was added 5-acetyl-1-(3-bromophenyl) benzimidazole (52) (1.5 g, 4.8 mmol) and (PPh$_3$)$_2$PdCl$_2$ (340 mg, 0.48 mmol) under argon. The reaction mixture was stirred at 80° C. for 24 hr in a 50 ml sealed tube. After cooling the mixture was concentrated, triturated with water (100 ml) and extracted with CH$_2$Cl$_2$ (200 ml×3). The extract was washed with brine, dried and concentrated under reduced pressure. The residue was washed with ether to afford crystalline (51) (1.5 g, 89%).

5-Acetyl-1-(3-bromophenyl)benzimidazole (52) was prepared as follows:

4-Acetyl-2-nitroaniline: N-(4-acetyl-2-nitrophenyl) acetamide (26.5 g, 11,94 mmol) was added to a mixture of water and concentrated sulfuric acid, 150 ml (1:2). After 15 minutes the mixture was poured into water. The product was filtered off, washed with water and dried.

N-(3-Bromophenyl)-4-acetyl-2-nitroaniline: A mixture of 4-acetyl-2-nitroaniline (3.41 g, 18.94 mmol), 1,3-dibromobenzene (4.6 ml, 38.06 mmol), potassium carbonate (2.62 g, 19 mmol) and a catalytic amount of copper bronze is heated with stirring to 180° C. under a stream of nitrogen for 2 days. After cooling the solid reaction cake is extracted with a mixture of dichloromethane and methanol (9:1). The extract is concentrated under reduced pressure. The residue is extracted with ethyl acetate. This extract is concentrated under reduced pressure and the residue is eluted through silica gel with a mixture of petroleum ether and ethyl acetate (4:1) to afford the pure product. Yield 0.67 g (10.6%). Mp. 142–144° C.

5-Acetyl-1-(3-bromophenyl)benzimidazole (52): N-(3-bromophenyl)-4-acetyl-2-nitroaniline (9.0 g, 26,63 mmol) was suspended in 99% ethanol (100 ml). Raney nickel was added and the mixture was hydrogenated at ambient pressure for 20 hours. Chloroform was added. The mixture was filtered through celite and evaporated in vacuo to afford 8.03 g oil. To this oil 80 ml formic acid was added and the mixture was heated to 80° C. for 1.5 hours. Excess formic acid was removed in vacuo. The residue was stirred in water and rendered alkaline with aqueous sodium hydroxide. The product was filtered off washed with water and dried.

EXAMPLE 19

5-Acetyl-1-(3-(2-thiazolyl)phenyl)benzimidazole O-methyl oxime (53): (51) from Example 18 (300 mg, 0.94 mmol) was added to a mixture of ethanol (5 ml), methoxylamine hydrochloride (300 mg, 3.5 mmol) and triethylamine (0.17 ml, 1.2 mmol) and the mixture was stirred at 60° C. for 0.5 hr. After cooling the mixture was poured into 5% aqueous NaHCO$_3$ (100 ml) and the precipitate was filtered off, washed with water, and dried under reduced pressure. The crude product was purified by column-chromatography on silica gel using a mixture of CH$_2$Cl$_2$ and methanol (100:1) as the eluent to give (53) (270 mg, 86%). Mp. 157–159° C.

EXAMPLE 20

5-Cyano-1-(3-(2-thiazolyl)phenyl)benzimidazole (54) was synthesized as described in Example 18 but using 5-cyano-1-(3-iodophenyl)benzimidazole (2.0 g, 5.9 mmol) instead of (52), (PPh$_3$)$_2$PdCl$_2$ (100 mg, 0.14 mmol) and (50) (3.6 g, 9.7 mmol). The reaction gave 5-cyano-1-(3-(2-thiazolyl)phenyl)benzimidazole (1.5 g, 86%).

5-cyano-1-(3-iodophenyl)benzimidazole was prepared as described below:

N-(3-Iodophenyl)-4-cyano-2-nitroaniline: To a solution of 4-chloro-3-nitrobenzonitril (1.82 g, 10 mmol) in dry DMF (25 ml) is added triethylamine (1.54 ml, 11 mmol) and 3-iodoaniline (1.2 ml, 10 mmol) and the mixture is heated to 80–100° C. over night. After cooling the mixture is poured into four volumes of ice-water. The precipitate is filtered off, washed with water and dried. This crude product is washed with hot ethanol to yield 2.1 g (58%) of the title compound. Mp. 211–212° C.

2-Amino-(N-(3-iodophenyl))-4-cyanoaniline: To a suspension of N-(3-Iodophenyl)-4-cyano-2-nitroaniline (2,1 g, 5.75 mmol) in methanol (50 ml) is added ammonium chloride (0.92 g, 17.25 mmol) and sodium sulfide nonahydrate (4.14 g, 17.25 mmol) and the mixture is heated to reflux for 1.5 hours. After cooling the mixture is poured into ice-water (200 ml) and the product is filtered off, washed with water and dried to leave 1.8 g (93%) of the title compound. Mp. 170–172° C.

5-Cyano-1-(3-iodophenyl)benzimidazole: A suspension of 2-amino-(N-(3-iodophenyl))4-cyanoaniline (1,8 g, 5.36 mmol) in formic acid (20 ml) is heated to 80–100° C. for 1.5 hours. The hot reaction mixture is filtered through a cotton pad into ice-water (100 ml). The precipitate is filtered off, washed with water and dried. This crude product is dissolved in dichloromethane and is brought to precipitation by addition of petroleum ether. The product is filtered off and dried. Yield: 1.38 g (75%) of the title compound. Mp. 177–179° C.

EXAMPLE 21

5-Formyl-1-(3-(2-thiazolyl)phenyl)benzimidazole (55): Raney Ni (2.0 g) was added to a solution of (54) (1.5 g, 4.9 mmol) in HCO$_2$H (18 ml) and water (6 ml). The mixture was stirred under argon at 110° C. for 1 hr. After cooling the mixture was filtered. The filtrate was concentrated, partitioned between a 5% aqueous NaHCO$_3$ solution and ethyl acetate. The organic phase was washed with brine, dried and concentrated under reduced pressure to give (55) (1.3 g, 87%).

EXAMPLE 22

5-Formyl-1-(3-(2-thiazolyl)phenyl)benzimidazole oxime: (55) (700 mg, 2.29 mmol) was added to a mixture of ethanol (25 ml) and NH$_2$OH.HCl (600 mg, 6.9 mmol). The mixture was stirred at 90° C. for 1 hr. After cooling the mixture was poured into water (100 ml) and the precipitate was filtered off, washed with water, and dried under reduced pressure to give 5-Formyl-1-(3-(2-thiazolyl)phenyl)benzimidazole oxime (690 mg, 94%).

5-Formyl-1-(3-(2-thiazolyl)phenyl)benzimidazole O-methyl oxime (56) was prepared analogously but using NH$_2$OMe.HCl instead of NH$_2$OH.HCl.Mp. 154–160° C.

EXAMPLE 23

4-(3-Nitrophenyl)pyrimidine (57): A mixture of 4-phenylpyrimidine (10 g, 64 mmol) and conc. H$_2$SO$_4$ (33 ml) was added to a mixture of conc. H$_2$SO$_4$ (22 ml) and conc. HNO$_3$ (16 ml) at 0° C. The resulting mixture was stirred at 0° C. for 2 hr, poured onto crushed ice, and extracted with CH$_2$Cl$_2$. The extract was washed with a 5% aqueous NaHCO$_3$ solution, dried over MgSO$_4$ and concentrated under reduced pressure. The residue was triturated with isopropanol and the precipitate was filtered off and dried under reduced pressure to give (57) (6.4 g, 50%).

EXAMPLE 24

4-(3-Aminophenyl)pyrimidine (58): To a suspension of (57) (6.3 g, 31 mmol) in a mixture of MeOH (60 ml) and THF (30 ml) was added 5% palladium on activated carbon (300 mg) and the mixture was hydrogenated at ambient pressure for 1 hr. The mixture was filtered and concentrated under reduced pressure. The residue was purified by column-chromatography on silica gel using a mixture of hexane and ethylacetate (3:1) as the eluent to give (58) (5.1 g, 96%).

EXAMPLE 25

N-(3-(4-pyrimidyl)phenyl)-4-cyano-2-nitroaniline (59): To a mixture of 4-chloro-3-nitrobenzonitril (5.5 g, 30 mmol) and (58) (5.1 g, 30 mmol) in THF (120 ml) was added sodium hydride (2.3 g, 50% suspension in mineral oil). After stirring at room temperature for 2 days, the mixture was poured into water and extracted with CH$_2$Cl$_2$. The extract was concentrated under reduced pressure and the residue was triturated with diethylether to yield crystalline (59) (9.2 g, 96%).

EXAMPLE 26

N-(3-(4-pyrimidyl)phenyl)-4-cyano-2-aminoaniline (60): was synthesized as described in Example 24 but using (59) (9.2 g, 29 mmol) instead of (57) and 600 mg catalyst. The reaction gave (60) (8.3 g, quant.)

EXAMPLE 27

5-Cyano-1-(3-(4-pyrimidyl)phenyl)benzimidazole (61): A mixture of (60) (3.0 g, 10 mmol) and HCO$_2$H (20 ml) was stirred at 110° C. for 1 hr. The mixture was concentrated in vacuo. The residue was partitioned between a 5% aqueous NaHCO$_3$ solution and CH$_2$Cl$_2$. The organic phase was dried over MgSO₄, and the solvent was removed by evaporation. The residue was triturated with ethyl acetate to afford crystalline (61) (2.6g, 85%).

EXAMPLE 28

5-Formyl-1-(3-(4-pyrimidyl)phenyl)benzimidazole (62): was synthesized as described in Example 21 using (61) (2.5 g, 8.4 mmol) instead of (54) and 1.5 g Raney-Ni. The reaction gave (62) (1.9 g, 73%).

EXAMPLE 29

5-Formyl-1-(3-(4-pyrimidyl)phenyl)benzimidazole oxime (63): was synthesized as described in Example 22 using (62) (150 mg, 0.50 mmol) instead of (55) and NH₂OH.HCl (100 mg, 1.5 mmol). The reaction gave (63) (120 mg, 76%).Mp. 220–221° C.

5-Formyl-1-(3-(4-pyrimidyl)phenyl)benzimidazole O-methyl oxime (64): was synthesized as described in Example 22 but using (62) (200 mg, 0.66 mmol) instead of (55) and NH₂OMe.HCl (250 mg, 2.0 mmol). The reaction gave (64) (61 mg, 28%). Mp. 180–182° C.

EXAMPLE 30

N-(3-(2-pyrimidyl)phenyl)-4-cyano-2-nitroaniline (65): was synthesized as described in Example 25 using 2-(3-aminophenyl)pyrimidine (4.50 g, 26.3 mmol) instead of (58). The reaction gave (65). (5.08 g, 61%).

EXAMPLE 31

N-(3-(2-pyrimidyl)phenyl)-4-cyano-2-aminoaniline (66): was synthesized as described in Example 24 but using (65) (1.2 g, 3.8 mmol) instead of (57).The reaction gave (66) (1.0 g, 93%).

EXAMPLE 32

5-Cyano-1-(3-(2-pyrimidyl)phenyl)benzimidazole (67): was synthesized as described in Example 27 using (66) (1.0 g, 3.5 mmol) instead of (60). The reaction gave (67) (840 mg, 80%).

EXAMPLE 33

5-Formyl-1-(3-(2-pyrimidyl)phenyl)benzimidazole (68): A solution of DIBAL-H in toluene (2.5 ml, 1.0 M) was added to a mixture of (67) (367 mg, 1.2 mmol) and CH₂Cl₂ (60 ml) at -78° C. The reaction mixture was stirred for 1 hr at -78° C. and for 1 hr at room temperature. A saturated NH₄Cl solution was added to the reaction mixture and stirring was continued for 0.5 hr. The mixture was poured into water and extracted with CH₂Cl₂. The organic extract was dried over MgSO₄, and the solvent was evaporated under reduced pressure to give (68) (142 mg, 38%).

EXAMPLE 34

5-Formyl-1-(3-(2-pyrimidyl)phenyl)benzimidazole O-methyl oxime (69): was synthesized as described in Example 22 but using (68) (210 mg, 0.70 mmol) instead of (55) and NH₂OMe.HCl (300 mg, 3.6 mmol) instead of NH₂OH.HCl. The reaction gave (69) (192 mg, 83%). Mp. 158–159° C.

The compounds prepared in the above examples are listed in the following Table 1:

TABLE 1

| Compound No. | X | R' | R" | M.p. | Example |
|---|---|---|---|---|---|
| 29d | 2-thienyl | methyl | hydrogen | 184–185° C. | 9 |
| 29b | 1-imidazolyl | methyl | hydrogen | 197–199° C. | 11 |
| 29c | 3-furanyl | methyl | hydrogen | 147–148° C. | 10 |
| 33a | 3-pyridyl | Ethyl | methyl | 105–106° C. | 14 |
| 33b | 3-pyridyl | 2-propynyl | methyl | 138–140° C. | 14 |
| 33c | 3-pyridyl | 2-propenyl | methyl | 87–89° C. | 14 |
| 33d | 5-pyrimidyl | ethyl | methyl | 187–188° C. | 14 |
| 33e | 2-pyridyl | ethyl | methyl | 107–108° C. | 14 |
| 33f | 3-pyridyl | iso-butyl | methyl | 90–92° C. | 14 |
| 33g | 3-pyridyl | methyl | methyl | 145–146° C. | 14 |
| 33h | 2-amino-5-pyrimidyl | methyl | methyl | 236–238° C. | 14 |
| 33i | 3-pyridyl | hydrogen | methyl | 218–220° C. | 14 |
| 33j | 3-pyridyl | iso-propyl | methyl | 77–80° C. | 15 |
| 38a | 1-imidazolyl | methyl | methyl | 230–231° C. | 14 |
| 38b | 1-imidazolyl | ethyl | methyl | 135–138° C. | 14 |
| 53 | 2-thiazolyl | methyl | methyl | 157–159° C. | 19 |
| 56 | 2-thiazolyl | methyl | hydrogen | 154–160° C. | 22 |
| 63 | 4-pyrimidyl | hydrogen | hydrogen | 220–221° C. | 29 |
| 64 | 4-pyrimidyl | methyl | hydrogen | 180–182° C. | 29 |
| 69 | 2-pyrimidyl | methyl | hydrogen | 158–159° C. | 354 |

We claim:

1. A compound having the formula:

or a pharmaceutically acceptable salt thereof or an oxide thereof
wherein
R³ is wherein
A, B and D are each CH, or N and
R¹¹ is phenyl, benzimidazolyl, or monocyclic heteroaryl, which may be unsubstituted or substituted one or more times with substitutents selected from the group consisting of alkyl, alkoxy, halogen, CF₃, amino, nitro, cyano, acylamino, acyl, phenyl and monocyclic heteroaryl; and one of R⁶ and R⁷ is hydrogen and the other is —CR'=NOR", wherein R' and R" each independently are hydrogen, alkyl, alkenyl, alkynyl or phenyl and wherein R' is not hydrogen when R" is hydrogen or alkyl.

2. A compound which is 1-(3(3-furanyl-phenyl)-5-formyl-benzimidazole O-methyl oxime; 5-acetyl-1-(3-(3-pyridyl)phenyl)benzimidazole O-ethyl oxime; 5-acetyl-1-(3-(3-pyridyl)phenyl)benzimidazole oxime; 5-acetyl-1-(3-(1-imidazolyl)phenyl)benzimidazole O-methyl oxime; 5-acetyl-1-(3-(1-imidazolyl)phenyl)benzimidazole O-ethyl oxime; or 5-acetyl-1-(3-(2-thiazolyl)benzimidazole O-methyl oxime; or a pharmaceutically acceptable salt thereof or an oxide thereof.

3. A compound which is 1-(3-(2-Thienyl)phenyl)-5-formylbenzimidazole O-methyl oxime; 1-(3-(1-Imidazolyl)phenyl)-5-formylbenzimidazole O-methyl oxime; 5-Acetyl-1-(3-(3-pyridyl)phenyl)benzimidazole O-propargyl oxime; 5-Acetyl-1-(3-(3-pyridyl)phenyl)benzimidazole O-allyl oxime; 5-Acetyl-1-(3-(3-pyridyl)phenyl)benzimidazole O-iso-butyl oxime; 5-Acetyl-1-(3-(3-pyridyl)phenyl) benzimidazole O-methyl oxime; 5-Acetyl-1-(3-(3-pyrimidyl)phenyl)benzimidazole O-ethyl oxime; 5-Acetyl-1-(3-(2-pyridyl)phenyl)benzimidazole O-ethyl oxime; 5-Acetyl-1-(3-(2-aminopyrimid-5-yl)phenyl)benzimidazole O-methyl oxime; 5-Acetyl-1-(3-(3-pyridyl)phenyl) benzimidazole O-iso-propyl oxime; 5-Formyl-1-(3-(2-thiazolyl)phenyl)benzimidazole; 5-Formyl-1-(3-(2-thiazolyl)phenyl)benzimidazole O-methyl oxime; 5-Formyl-1-(3-(4-pyrimidyl)phenyl)benzimidazole oxime; 5- Formyl-1-(3-(4-pyrimidyl) phenyl)benzimidazole O-methyl oxime; or 5-Formyl-1-(3-(2-pyrimidyl)phenyl) benzimidazole O-methyl oxime; or a pharmaceutically acceptable salt thereof or an oxide thereof.

4. A pharmaceutical composition comprising an effective amount of a compound of any of claims 1–3 or a pharmaceutically acceptable salt thereof or an oxide thereof together with at least one pharmaceutically acceptable carrier or diluent.

5. A method of treating a disorder or disease of a living animal body, which disorder or disease is responsive to modulation of the GABA_A receptor complex of the central nervous system comprising administering to such a living animal body in need thereof a therapeutically-effective amount of a compound of any of claims 1–3.

6. The method as in claim 5, wherein said disorder or disease is responsive to positive modulation of the GABA_A receptor complex.

7. The method as in claim 5, said disease is selected from the group consisting of anxiety, sleep disorders, memory disorders and epilepsy.

8. The method as in claim 5, wherein the active ingredient is administered in the form of a pharmaceutical composition thereof, in which it is present together with a pharmaceutically-acceptable carrier or diluent.

9. A method of modulating a GABA_A receptor complex comprising exposing said receptor complex to an effective amount of a compound of any of claims 1–3.

10. The pharmaceutical composition of claim 4, wherein the compound is present in 0.01–100 20 mg/unit dosage.

11. The method of claim 5, wherein said disease is a convulsive disorder.

12. The method of claim 5, wherein said living animal body is a human.

13. A method of making a compound of claim 1 comprising using a sythesis scheme selected from the following schemes a–d:

c)

d)

wherein Hal is halogen; alk is alkyl and A, B, D, R', R" and $R^{11}$ are as defined in claim 11.

14. The method of claim 13 further comprising resolving racemic forms of the compounds into optical isomers.

* * * * *